United States Patent
Maneshin et al.

[11] Patent Number: 6,106,718
[45] Date of Patent: Aug. 22, 2000

[54] ENHANCED DENITRIFICATION PROCESS BY MONITORING AND CONTROLLING CARBONACEOUS NUTRIENT ADDITION

[75] Inventors: Sergey K. Maneshin, Upper Holland; Xin Yang, Holland; Jaw Fang Lee, Berwyn, all of Pa.

[73] Assignee: BioChem Technology, Inc., King of Prussia, Pa.

[21] Appl. No.: 09/343,640

[22] Filed: Jun. 30, 1999

Related U.S. Application Data

[60] Provisional application No. 60/091,462, Jul. 1, 1998.

[51] Int. Cl.[7] .............................. C02F 3/00; G01N 33/487
[52] U.S. Cl. ........................... 210/614; 210/903; 436/110
[58] Field of Search .................................... 210/605, 614, 210/620, 631, 903, 906, 96.1; 436/172, 110, 114, 115

[56] References Cited

U.S. PATENT DOCUMENTS

| | | | |
|---|---|---|---|
| 3,348,409 | 10/1967 | Arthur | 73/19 |
| 3,354,057 | 11/1967 | Klingelhoefer | 204/1 |
| 3,374,065 | 3/1968 | Suzuki | 23/253 |

(List continued on next page.)

FOREIGN PATENT DOCUMENTS

| | | |
|---|---|---|
| 0 461 166 B1 | 6/1994 | European Pat. Off. . |
| 3811540 A1 | 10/1989 | Germany . |
| 59-99353 | 6/1984 | Japan . |
| 662579 | 5/1979 | U.S.S.R. . |
| 2 184 110 | 6/1987 | United Kingdom . |
| WO 90/10083 | 9/1990 | WIPO . |
| WO 93/23738 | 11/1993 | WIPO . |
| WO 95/03254 | 2/1995 | WIPO . |
| WO 97/26525 | 7/1997 | WIPO . |

OTHER PUBLICATIONS

Anaerobic Subsurface Soil Microcosms: Methods to Monitor Effects of Organic Pollutants on Indigenous Microbial Activity, Joel M. Dougherty and Guy R. Lanza, *Toxicity Assessment: An International Journal*, vol. 4, 85–104 (1989).

A Bacterial Population Analysis of Granular Sludge From An Anaerobic Digester Treating a Maize–Processing Waste, A.R. Howgrave–Graham, F.M. Wallis and P.L. Steyn, *Bioresource Technology*, 37 (1991) 149–156.

The Effects of Nitrates and Carbon Compounds on Enhanced Biological Phosphorus Removal From Wastewaters, S. Ghekiere, H. Bruynooghe, K. Van Steenbergen, L. Vriens, A. Van Haute and H. Verachtert, *European Water Pollution Control*, vol. 1, No. 4, 1991.

Biological Oxygen Demand (BOD) Monitoring by a Multiprocessing System, George Hassapis, *IEEE Transactions on Instrumentation and Measurement*, vol. 40 No. 6, Dec. 1991.

Effects of Oxygen Transport Limitation on Nitrification in the Activated Sludge Process, Michael K. Stenstrom and Stephen S. Song, *Research Journal WPCF*, vol. 63, No. 3.

Continuous Estimation of Short Term Oxygen Demand From Respiration Measurements, H. Spanjers and A. Klapwijk, *Wat. Sci. Tech.*, vol. 24, No. 7, pp. 29–32, 1991.

(List continued on next page.)

*Primary Examiner*—Thomas G. Wyse
*Attorney, Agent, or Firm*—Schnader Harrison Segal & Lewis

[57] ABSTRACT

A method of determining denitrification time for at least a portion of wastewater in a wastewater treatment process including isolating a wastewater sample from the wastewater in the wastewater treatment process; detecting changes in fluorescence emitted by NADH from microorganisms contained within the sample; detecting changes in pH of the sample; analyzing the changes in NADH and pH and establishing that the sample is denitrified at a point where NADH shifts from a steady state or a decreasing state to an increasing state and, substantially simultaneously, the pH shifts from a steady state or an increasing state to a decreasing state; and calculating elapsed time between when the sample was taken and when the sample was denitrified to determine the denitrification time for the portion of the wastewater treatment process.

6 Claims, 10 Drawing Sheets

U.S. PATENT DOCUMENTS

| | | | |
|---|---|---|---|
| 3,510,406 | 5/1970 | Stack, Jr. | 204/1 |
| 3,565,583 | 2/1971 | McNulty et al. | 23/230 |
| 3,616,273 | 10/1971 | Oita | 204/1 |
| 3,760,829 | 9/1973 | Schuk et al. | 137/93 |
| 3,811,777 | 5/1974 | Chance | 356/73 |
| 3,877,875 | 4/1975 | Jones et al. | 23/230 |
| 3,925,721 | 12/1975 | Petroff | 210/2 |
| 3,926,737 | 12/1975 | Wilson et al. | 195/108 |
| 4,112,741 | 9/1978 | Kerfoot et al. | 73/53 |
| 4,162,195 | 7/1979 | Solyom et al. | 210/96.1 |
| 4,209,299 | 6/1980 | Carlson | 23/230 R |
| 4,216,065 | 8/1980 | Rechnitz et al. | 204/1 T |
| 4,220,715 | 9/1980 | Ahnell | 435/34 |
| 4,246,101 | 1/1981 | Selby, III | 210/615 |
| 4,260,490 | 4/1981 | Moss et al. | 210/620 |
| 4,277,343 | 7/1981 | Paz | 210/614 |
| 4,288,229 | 9/1981 | Mar | 23/230 PC |
| 4,297,173 | 10/1981 | Hikuma et al. | 204/17 |
| 4,385,113 | 5/1983 | Chappelle et al. | 435/8 |
| 4,427,772 | 1/1984 | Kodera et al. | 435/27 |
| 4,488,814 | 12/1984 | Johnson | 356/414 |
| 4,537,682 | 8/1985 | Wong-Chong | 210/611 |
| 4,554,077 | 11/1985 | Brown et al. | 210/656 |
| 4,564,444 | 1/1986 | Hiraoka et al. | 210/96.1 |
| 4,564,453 | 1/1986 | Coplot et al. | 210/614 |
| 4,577,110 | 3/1986 | MacBride et al. | 250/461.2 |
| 4,631,530 | 12/1986 | Gasper | 340/679 |
| 4,666,610 | 5/1987 | Kuhns | 210/749 |
| 4,793,930 | 12/1988 | Soeder et al. | 210/614 |
| 4,818,408 | 4/1989 | Hamamoto | 210/614 |
| 4,845,025 | 7/1989 | Lary et al. | 435/2 |
| 4,849,330 | 7/1989 | Humphries et al. | 435/4 |
| 4,999,116 | 3/1991 | Bowers | 210/709 |
| 5,013,442 | 5/1991 | Davis et al. | 210/614 |
| 5,094,752 | 3/1992 | Davis et al. | 210/614 |
| 5,118,626 | 6/1992 | Hashimoto et al. | 435/289 |
| 5,173,187 | 12/1992 | Nader et al. | 210/614 |
| 5,180,494 | 1/1993 | Yamaguchi et al. | 210/603 |
| 5,266,209 | 11/1993 | Knight et al. | 210/691 |
| 5,389,524 | 2/1995 | Larsen et al. | 435/29 |
| 5,397,473 | 3/1995 | Jewell | 210/903 |
| 5,401,412 | 3/1995 | Yang et al. | 210/614 |
| 5,466,604 | 11/1995 | Yang et al. | 435/286.1 |
| 5,506,096 | 4/1996 | Helmo | 210/614 |
| 5,552,319 | 9/1996 | Yang et al. | 435/286.5 |
| 5,580,791 | 12/1996 | Thorpe et al. | 436/172 |
| 5,629,202 | 5/1997 | Su et al | 435/286.5 |
| 5,641,966 | 6/1997 | Karlberg et al. | 258/373 |
| 5,658,802 | 8/1997 | Hayes et al. | 436/518 |
| 5,698,412 | 12/1997 | Lee et al. | 210/614 |
| 5,702,951 | 12/1997 | Bridger | 210/614 |
| 5,759,860 | 6/1998 | Smith et al. | 436/110 |
| 5,856,119 | 1/1999 | Lee et al. | 436/62 |
| 5,906,746 | 5/1999 | Helmo et al. | 210/614 |

OTHER PUBLICATIONS

The Applied Microbiology of Enhanced Biological Phosphate Removal—Accomplishments and Needs, D. Jenkins and V. Tandoi, *Wat. Res.*, vol. 25, No. 12, pp. 1471–1478, 1991.

Denitrification Unit Biocenosis, A. Grabińska–Loniewska, *Wat. Res.*, vol. 25, No. 12, pp. 1565–1573, 1991.

Analysis of Techniques for Evaluating and Optimizing Existing Full–Scale Wastewater Treatment Plants, G.T. Daigger, J.A. Buttz and J.P. Stephenson, *Wat. Sci. Tech.*, vol. 25, No. 4–5, pp. 103–118, 1992.

Characterization of Functional Microorganism Groups and Substrate in Activated Sludge and Wastewater by AUR, NUR and OUR, G. Holm Kristensen, P. Elberg Jårgensen and M. Henze, *Wat. Sci. Tech.*, vol. 25, No. 6, pp. 43–57, 1992.

Metabolism of Organic Substances in Anaerobic Phase of Biological Phosphate Uptake Process, Tomonori Matsuo, Takashi Mino and Hiroyasu Sato, *Wat. Sci. Tech.*, vol. 25, No. 6, pp. 83–92, 1992.

Biochemical Models for Phosphate Accumulating Microorganisms, Ma. del Carmen Doria–Serrano, S. Gonzálex––Martínez and M. Hernández–Esparza, *Wat. Sci. Tech.*, vol. 26, No. 9–11, pp. 2245–2248, 1992.

Aerobic Biodegradation and Microgial Population of a Synthetic Wastewater in a Channel with Suspended and Attached Biomass, Y.S. Cao and G.J. Alaerts, *Wat. Sci. Tech.*, vol. 31, No. 7, pp. 181–189, 1995.

Alkalinity Tells All Real–Time Control for the Entire Process, A.J. Freed and K.F. Davis, *Operations Forum*, Feb. 1994.

ENHANCED DENITRIFICATION PROCESS BY MONITORING AND CONTROLLING CARBONACEOUS NUTRIENT ADDITION

This application claims benefit of provisional application Ser. No. 60/091,462, filed Jul. 1, 1998.

FIELD OF THE INVENTION

The present invention relates to a method of monitoring and controlling the treatment of wastewater, more particularly, to a real time method of monitoring and controlling denitrification in a wastewater treatment process by maximizing the efficiency of carbonaceous nutrient addition.

BACKGROUND OF THE INVENTION

The prior art has employed many devices and systems to process and purify water from industrial operations and municipal sources prior to discharging the water. Activated-sludge wastewater treatment plants (WWTP's), which are well known in the art, have been most often utilized to address this problem. Additionally, many industrial and municipal water treatment plants utilize biological systems to pre-treat their wastes prior to discharging into the usual municipal treatment plant.

Microorganisms used in the activated sludge break down or degrade contaminants for the desired water treatment in these processes. Efficient process performance and control requires quick and accurate assessment of information on the activity of the microorganisms. This has proven to be a difficult task in view of the wide variety of materials and contaminants that typically enter into treatment systems. Also, variations in the quantity of wastewater being treated, such as daily, weekly or seasonal changes, can dramatically change numerous important factors in the treatment process, such as pH, temperature, dissolved oxygen, nutrients and the like, alteration of which can be highly detrimental to proper wastewater treatment. Improperly treated wastewater poses serious human health dangers.

Various biological nutrient removal (BNR) processes are often used in wastewater treatment plants to assist in contaminant degradation. In a typical BNR process, contaminants in the wastewater, such as carbon sources (measured as biochemical oxygen demand or BOD), ammonia, nitrates, phosphates and the like are digested by the activated sludge in anaerobic, anoxic and aerobic (oxic) stages, also known in the art. In the biological treatment process, the wastewater, with or without passing through a preliminary settlement process, is mixed with return activated sludge (RAS) from the final clarifiers. The microorganisms suspended in the wastewater, sometimes hereinafter referred to as "mixed liquor", then flow through the biological treatment process that may include one or all three anaerobic, anoxic and aerobic stages for proper nutrient removal.

As mentioned above, it is important to remove nitrogenous contaminants, which is performed in nitrification/denitrification processes. Biological removal of nitrogenous contaminants from wastewater involves two-step distinctive treatment processes: biological nitrification where ammonia-nitrogen is converted into nitrogen oxides such as nitrate and nitrite and biological denitrification where nitrate and nitrite are converted into nitrogen gas and released into the atmosphere. The following reactions represent the nitrogen removal in a typical wastewater treatment process:

  (1)

  (2)

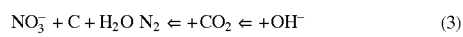  (3)

From the nitrogen removal point of view, denitrification is the process where nitrogen is finally removed from wastewater. In a typical wastewater treatment plant, nitrification is achieved in the aerobic process where oxygen is provided through aeration, and denitrification is achieved in anoxic process where oxygen is limited or absence. To achieve denitrification, either a certain fraction of nitrified mixed liquor is recycled to the front anoxic zone before the wastewater flows to the aerobic zone or the nitrified mixed liquor flows to a downstream anoxic zone before discharge to final clarifiers. A combination of internal recycle to the front anoxic zone and secondary anoxic zone that follows the aerobic zone is also a common practice in achieving total nitrogen removal.

In most wastewater treatment processes, nitrification is achieved in the aerobic zone where carbonaceous contaminants have been fully oxidized. The mixed liquor leaving the aerobic zone contains very limited amounts of carbonaceous contaminants. While this is a desirable treatment result as far as carbonaceous biochemical oxygen demand (C-BOD) removal is concerned, it is not a favorable condition to achieve further denitrification. Referring to reaction (3), denitrification requires not only the absence of oxygen, but also the supply of carbonaceous nutrient. The carbonaceous nutrient can be either biodegradable organic material in the water phase or intracellular stored nutrients inside the microorganisms that perform the denitrification.

When carbonaceous nutrient is severely limited, the microorganisms are in endogenous metabolic state and denitrification activity will be very low compared with the condition where carbonaceous nutrient is not limited. It has been a well known practice to feed the microorganisms carbonaceous nutrient to promote denitrification, especially after the aeration process. Methanol, among other organic compounds such as acetic acid and ethanol, is one common chemical used as a nutrient for the enhancement of denitrification because of its relatively low cost and high energy density. Nonetheless, it is important to monitor and control carbonaceous nutrient enhanced biological denitrification processes to maximize wastewater treatment quality and efficiency.

OBJECTS OF THE INVENTION

It is an object of the present invention to provide a method for monitoring denitrification in wastewater treatment systems during the anoxic stage.

It is a further object of the present invention to provide a method for real-time measuring the metabolic state of the microorganisms in wastewater to enhance control of denitrification in the anoxic stage of a wastewater treatment process, to maximize process performance in response to transient and other conditions.

Other objects of the present invention will be apparent to those of ordinary skill in the art based on the following drawings, detailed description of preferred embodiments and the appended claims.

SUMMARY OF THE INVENTION

The invention relates to a process for enhancing denitrification in a wastewater treatment system. The process includes first collecting a mixed liquor sample from the wastewater treatment tank or channel in the anoxic zone. The mixed liquor sample is analyzed and the NADH fluorescence and pH signals received from respective NADH and pH probes are used to determine the time required for total denitrification. Then, the sample is discharged to the treatment tank and a fresh sample is collected for the next analysis. According to the analysis result, the carbonaceous nutrient feeding rate to the anoxic reactor is adjusted (increase or decrease or maintain constant feeding rate) so that denitrification and carbonaceous nutrient consumption finish simultaneously when the mixed liquor leaves the anoxic reactor, achieving optimized denitrification.

DETAILED DESCRIPTION OF THE INVENTION

Figure 1:
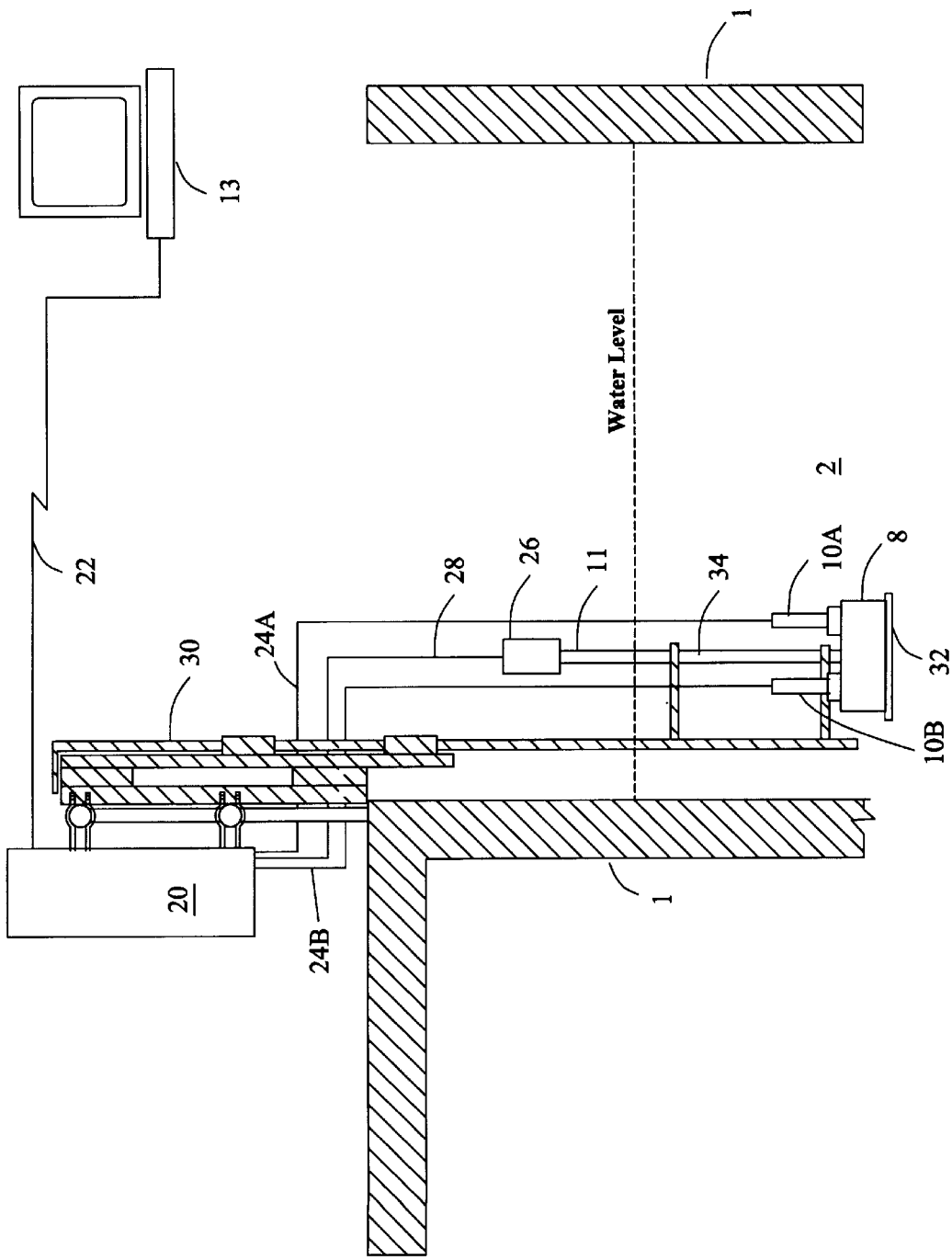
FIG. 1 is a schematic of the monitoring system of a typical wastewater treatment process utilizing embodiments of the invention.

The following description is intended to refer to specific embodiments of the invention illustrated in the drawings and is not intended to define or limit the invention, other than in the appended claims.

In order to effectively control the operation of the BNR process, it is necessary to regulate specific process parameters based upon the biological activity of the microorganisms in the anaerobic, anoxic and/or oxic stages of the treatment. Wastewater treatment plants are often subjected to severe transient conditions, such as diurnal variations in organic loads.

The proper evaluation and control of a complex BNR process as it applies to denitrification requires an accurate and current assessment of the metabolic state of the microorganisms in the mixed liquor, among other things, in a variety of environments and under a number of conditions.

The apparatus for controlling carbonaceous nutrient addition can be used in all stages of a WWTP or any combination thereof. Incorporation of the apparatus into a typical WWTP is shown schematically in FIG. 1. Measurements may be taken at any point or location in the system shown in FIG. 1. This includes multiple measurement locations within a selected stage, if desired. The general application and use of the apparatus in the anaerobic, anoxic and/or aerobic stages of a typical wastewater treatment plant will now be discussed.

Figure 2:
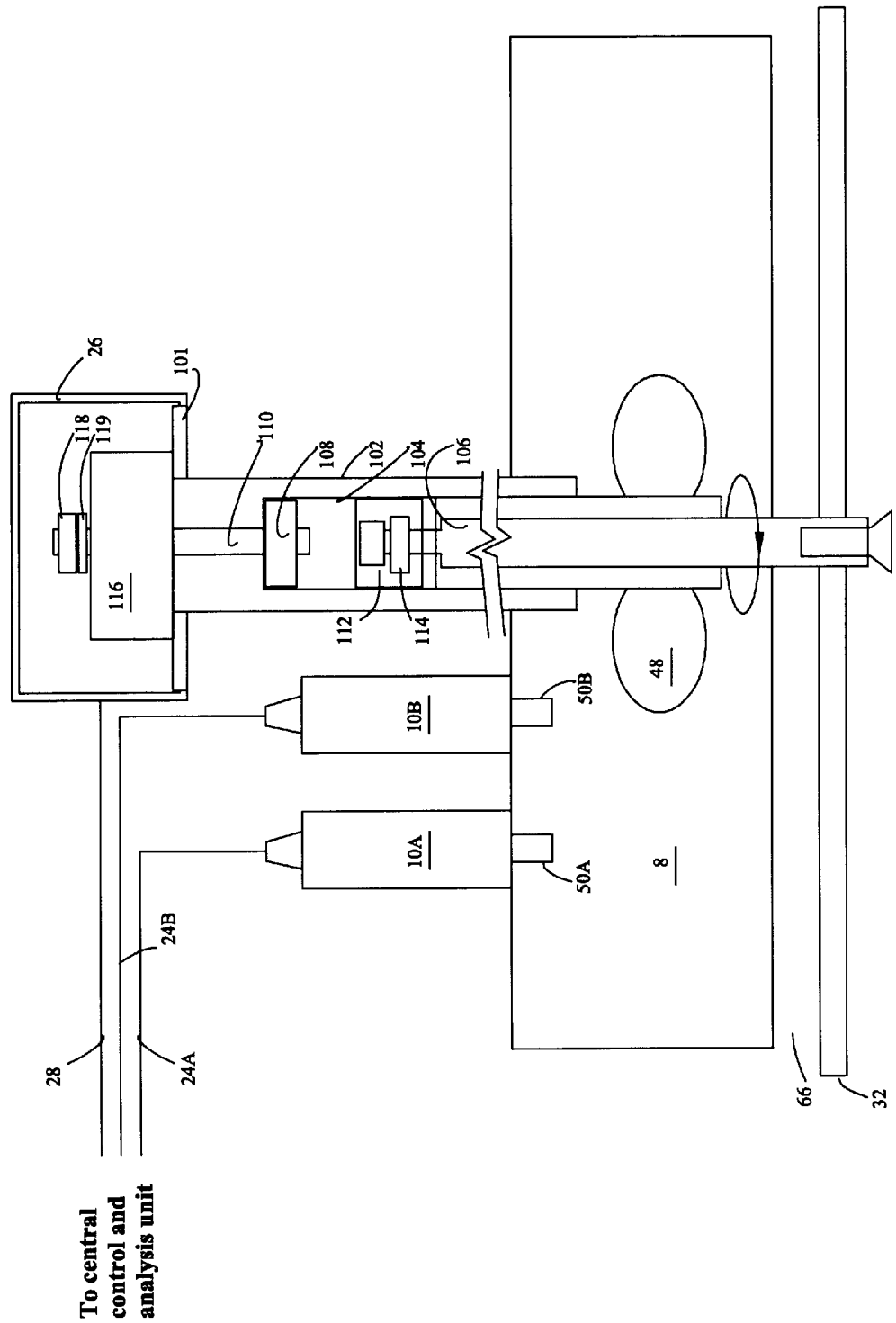
FIG. 2 shows a schematic front elevational view of an embodiment of apparatus of the invention used to monitor a bioreactor tank.

One embodiment of apparatus used for sampling wastewater that is analyzed in accordance with monitoring and controlling is shown in FIGS. 1 and 2. A bioreactor tank 1 (or, alternatively, a wastewater channel) contains wastewater 2 and sludge. Detection apparatus is mounted on the top of bioreactor tank 1 and extends into wastewater 2. The apparatus includes a central control unit 20 connected to a computer/monitor 13 by wire or wireless connection 22. Similarly, central control unit 20 connects to detection probes 10A and 10B by way of wire connections 24. Motor container 26 also connects to central control unit 20 by way of connection wire 28. Power is supplied to motor container 26 also by wire connection 28.

Detection probes 10A and 10B are positioned in detection chamber 8 and electrically connected to the central control unit 20 to detect changes in NADH fluorescence and changes in pH in wastewater samples. A preferred probe 10 for measuring NADH is disclosed in U.S. Pat. No. 4,577,110 and manufactured by BioChem Technology, Inc. of King of Prussia, Pa. A preferred pH probe 10 is manufactured by Sensorex. Of course, other apparatus can be employed as probes so long as the same or similar detection capabilities are available. Computer/monitor 13 may be of any suitable type such as a personal computer or the like.

Sampling unit 11 is mounted onto a movable carriage 30 which is capable of moving substantially vertically upwardly and downwardly to move the detection probes into and out of wastewater 2. The precise structure of movable carriage 30 is not critical so long as the preferred capability or movability of sampling unit 11 is achieved.

Detection probes 10 have their detection ends 50A and 50B located in detection chamber 8 as shown in FIG. 2. Detection chamber 8 has an opening 66 and an adjacent movable cover 32 which moves vertically upwardly and downwardly along guide channels 34 and closes or seals opening 66.

FIG. 2 shows detection chamber 8 having a detection probe 10A with a detection end 50A. Detection probe 10A is a pH probe. Detection chamber 8 also has a detection probe 10B with a detection end 50B. Detection probe 10B is an NADH probe. Propeller 48 is located interiorly of detection chamber 8 and stirs or agitates samples when probes 10A and 10B are in operation. Cover 32 is in a closed position which covers opening 66 (as shown in FIG. 1).

Propeller 48 is connected to motor container 26 by way of a series of coaxial tubes 102, 104 and 106. A nut 108 and a thrust bearing sleeve 112 are contained in and attached to middle tube 104. Outside tube 102 is mounted to base 101. Nut 108 is axially movable along threaded rod 110 to either open or close cover 32 depending on motor direction of motor 116. Nut 108 travels axially only if induced drag on middle tube 104 exceeds an amount of torque required for nut 108 to turn on threaded rod 110. This drag can be induced by propeller 48 attached to middle tube 104 and/or any bushings or other hardware in contact with middle tube 104. Thrust bearing sleeve 112 holds bearing 114 which carries axial tension of central tube 106 when cover 32 is closed. Bearing 114 allows middle tube 104 to rotate independently of central tube 106 and transfers axial motion of middle tube 104 to central tube 106. Outside tube 102 supports both motor container 26 and chamber 8 while protecting the internal parts. Chamber 8 is substantially sealed to outside tube 102 and when cover 32 is pulled against chamber 8 the space inside chamber 8 is sealed.

When motor 116 rotates in one direction nut 108 travels away from the motor, pushing cover 32 open. When nut 108 reaches stop 118, nut 108 no longer travels axially and this causes middle tube 104 to substantially match the motor speed. Chamber 8 is then in an open condition and propeller 48 induces an exchange of fluid between the inside and outside of chamber 8.

When motor 116 and threaded rod 110 rotate in the opposite direction nut 108 travels toward the motor, pulling cover 32 closed. When chamber 8 is closed, axial motion of nut 108 is prevented by tension on nut 108. This causes middle tube 104 to rotate at the same speed as motor 116 and threaded rod 110. Chamber 8 is then in a closed position so that fluid is retained inside chamber 8 while being constantly mixed by propeller 48.

We discovered that in a wastewater treatment process, when the microorganisms are subject to an environment with very limited carbonaceous nutrient available, the microorganisms enter an endogenous metabolic state where the intracellular NADH level decreases to a very low level. This is indicated by the low fluorescence measured by the NADH fluorescence probe. In the endogenous state, when a certain amount of carbonaceous nutrient is provided to the microorganisms, the NADH level increases significantly due to the increased activity of carbonaceous metabolism. This is true under aerobic conditions regardless of the microorganisms where the dissolved oxygen level in the water phase is higher than 0.2 ppm, or under anoxic conditions where dissolved oxygen is absent, but nitrate or nitrite is present, or under anaerobic conditions where both oxygen and nitrate and nitrite are absent.

The stepwise increase of fluorescence intensity from the microorganisms due to the feeding of carbonaceous nutrient can be differentiated from the stepwise change of fluorescence intensity due to the metabolic state change from aerobic to anoxic or from anoxic to anaerobic condition.

Figure 3:
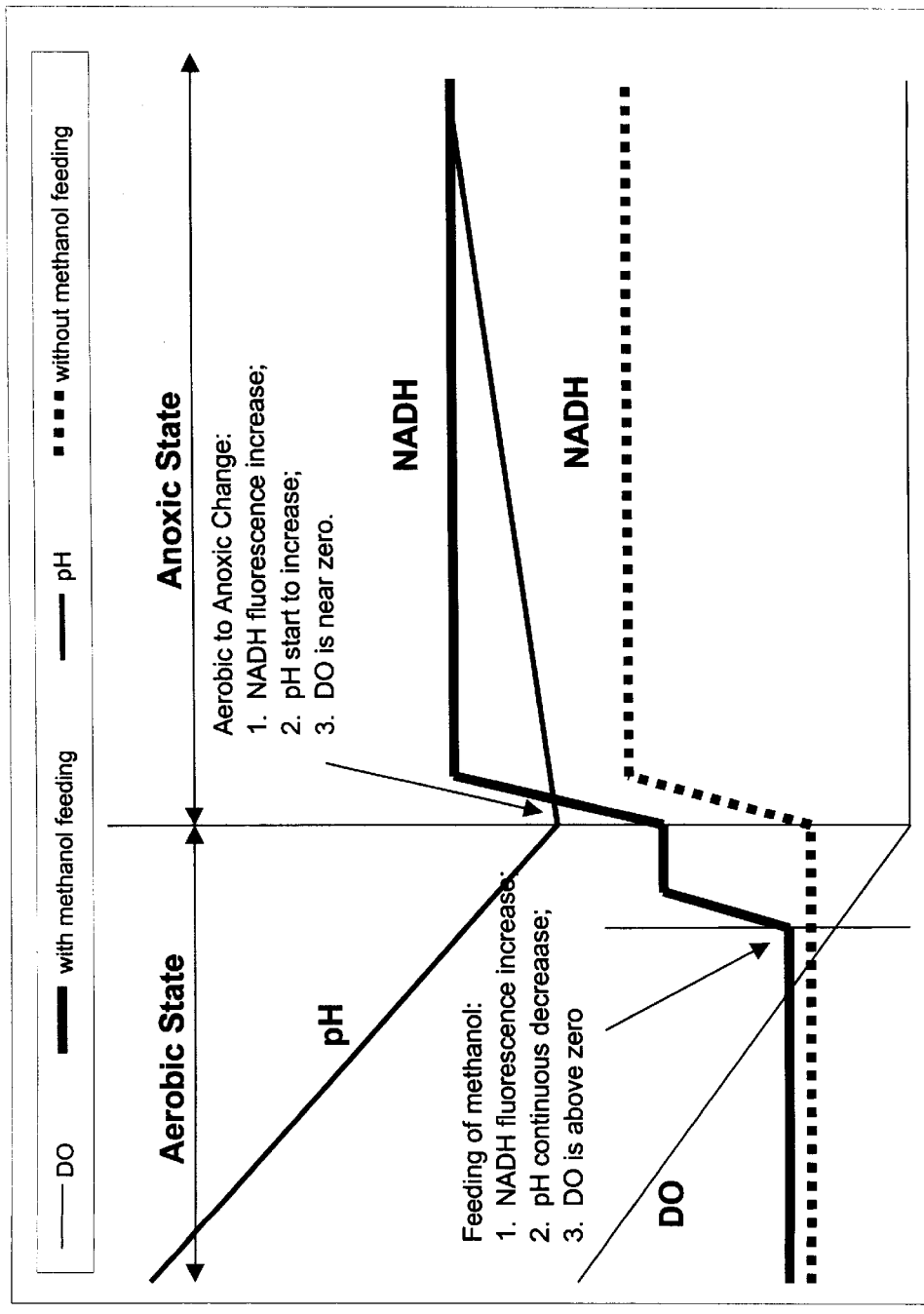
FIG. 3 is a graph of NADH, pH and D.O. versus time in the aerobic and anoxic states of a typical wastewater treatment process.

Under aerobic conditions, the NADH fluorescence increase due to carbonaceous nutrient feeding is associated with the non-zero level of dissolved oxygen concentration measured by a DO probe and a continuous decrease in pH measured by a pH probe, while the fluorescence change due to metabolic state change from aerobic to anoxic is accompanied by a near zero level of dissolved oxygen and a start of a pH increase. This is schematically represented in FIG. 3. The amount of dissolved oxygen can be determined by any means known in the art such as described in U.S. Pat. No. 5,698,412.

Figure 4:
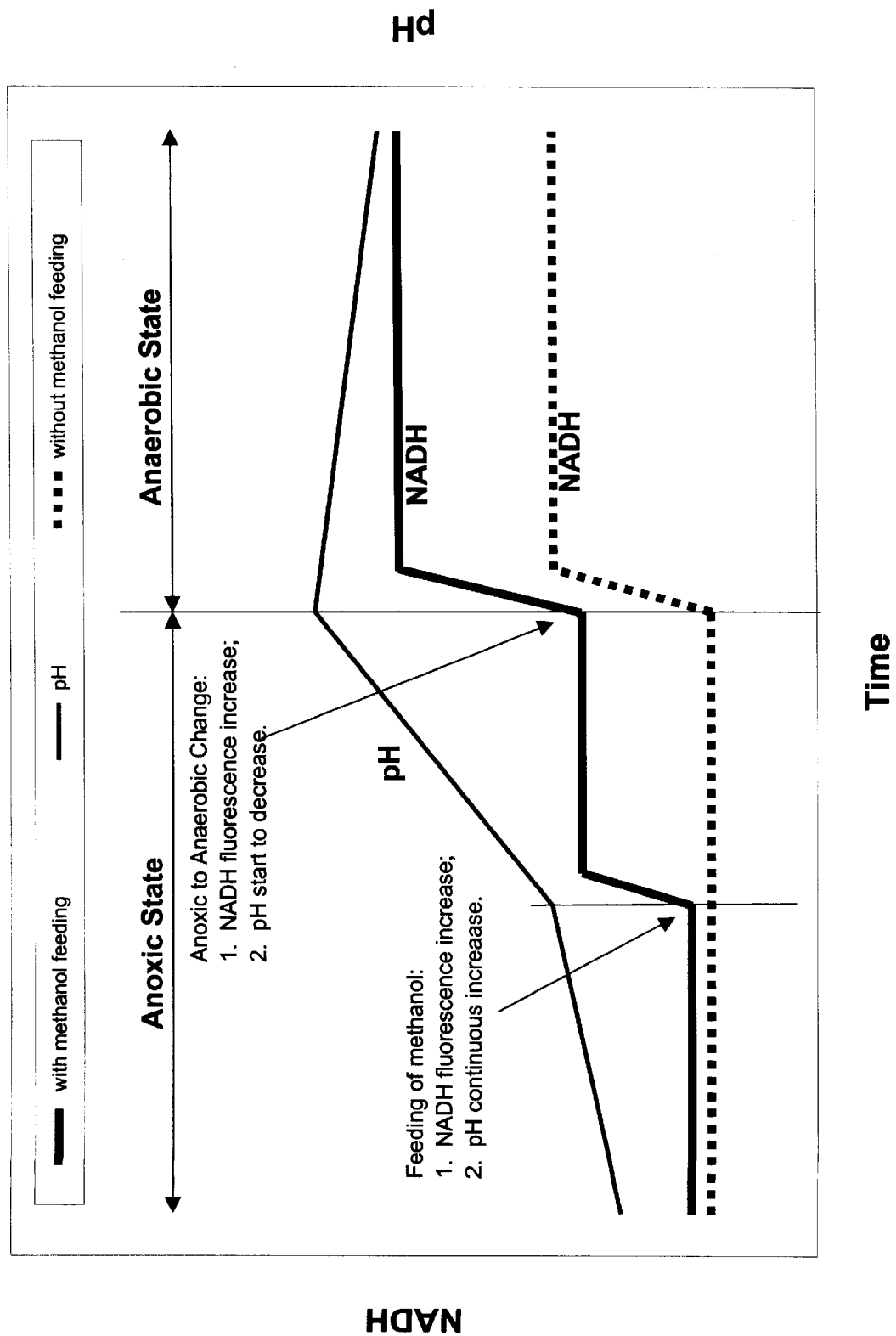
FIG. 4 is a graph of NADH and pH versus time in the anoxic and anaerobic states of a typical wastewater treatment process.
Figure 5:
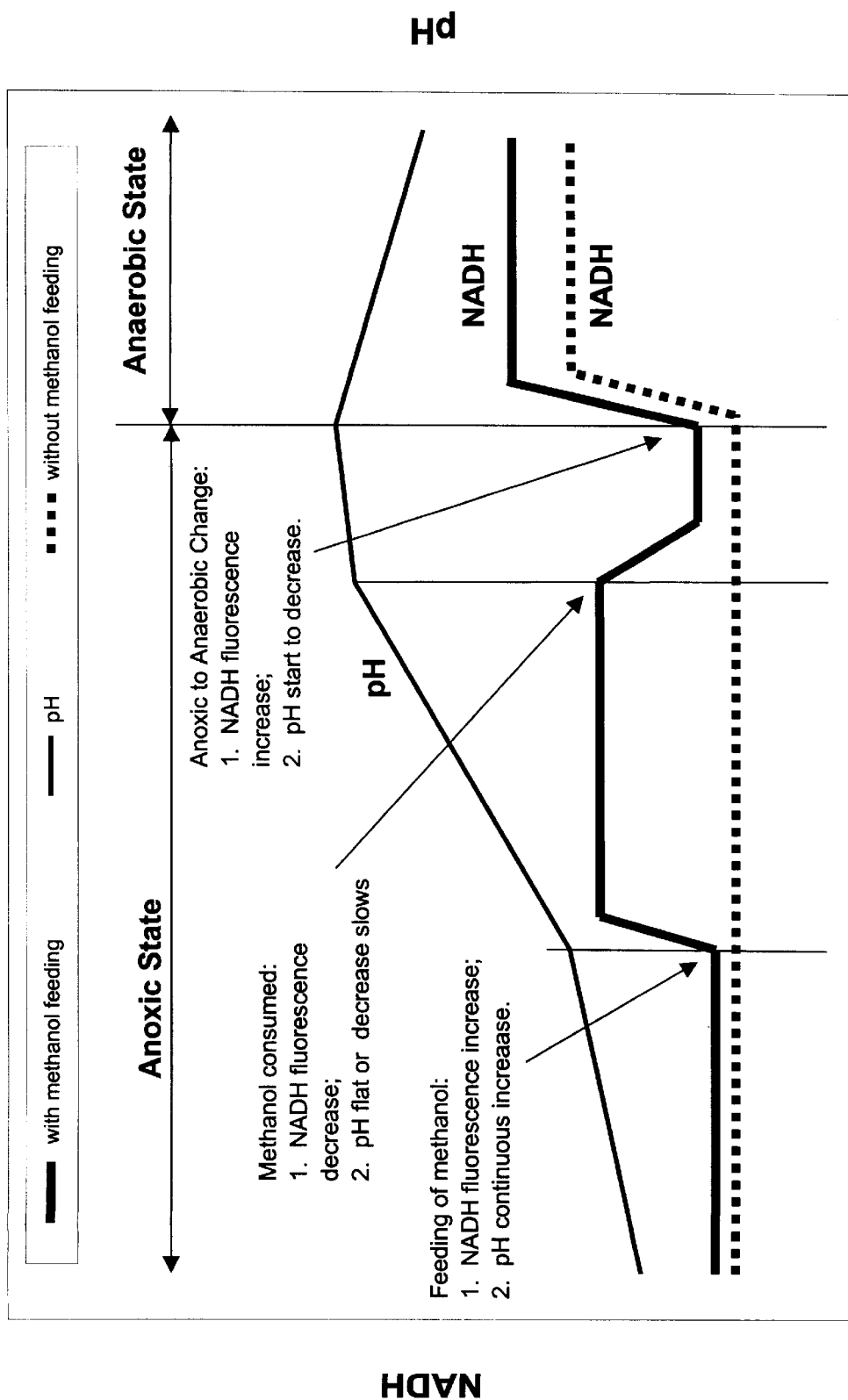
FIG. 5 is a graph of NADH and pH versus time in the anoxic and anaerobic states of a typical wastewater treatment process.

Under anoxic conditions, the stepwise fluorescence intensity increases due to carbonaceous nutrient feeding is characterized by a continuous increase in pH, while the fluorescence change due to metabolic state change from anoxic to anaerobic is indicated by a start of a decrease in pH, as represented in FIG. 4. On the other hand, when the added carbonaceous nutrient is consumed by the microorganisms, the NADH fluorescence gives a stepwise decrease accompanied by a slow down or total stop of pH increase, as represented in FIG. 5.

Figure 6:
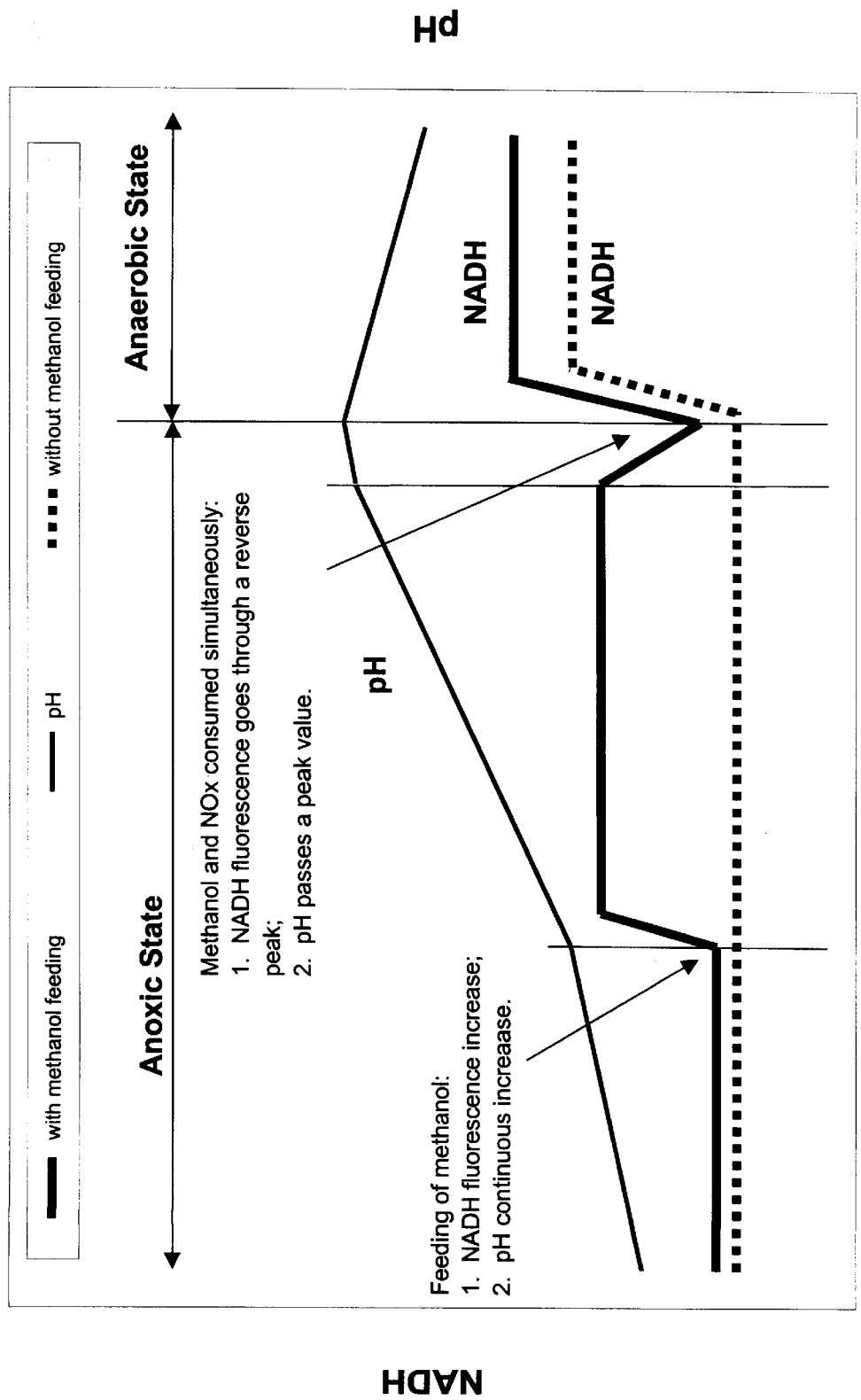
FIG. 6 is a graph of NADH and pH versus time in the anoxic and anaerobic states of a typical wastewater treatment process.

We discovered that the combined measurement of pH and NADH fluorescence provides a sensitive method for monitoring carbonaceous nutrient addition to enhance denitrification processes. In an enhanced denitrification process by carbonaceous nutrient addition, the objective is to control the amount of carbonaceous nutrient addition to the microorganisms so that the denitrification finishes at the same time that the carbonaceous nutrient is totally consumed as the mixed liquor exists the anoxic zone. The conditions where chemicals were wasted by over feeding or denitrification was not finished in the anoxic stage due to underfeeding can be avoided by proper monitoring and control of carbonaceous nutrient addition. The enhanced denitrification process brought about by monitoring and controlling carbonaceous nutrient addition is represented in FIG. 6.

A typical monitoring and control operation of the invention consists of the following basic steps:

1) collect a mixed liquor sample from the wastewater treatment tank or channel in the anoxic zone;
2) analyze the NADH fluorescence and pH signals received from the respective NADH and pH probes and determine the time required for total denitrification;
3) according to the analysis result, adjust the carbonaceous nutrient feeding rate to the tank or channel so that denitrification and carbonaceous nutrient consumption finish simultaneously; and
4) discharge the sample to the treatment tank and collect a fresh sample for the next analysis.

Figure 7:
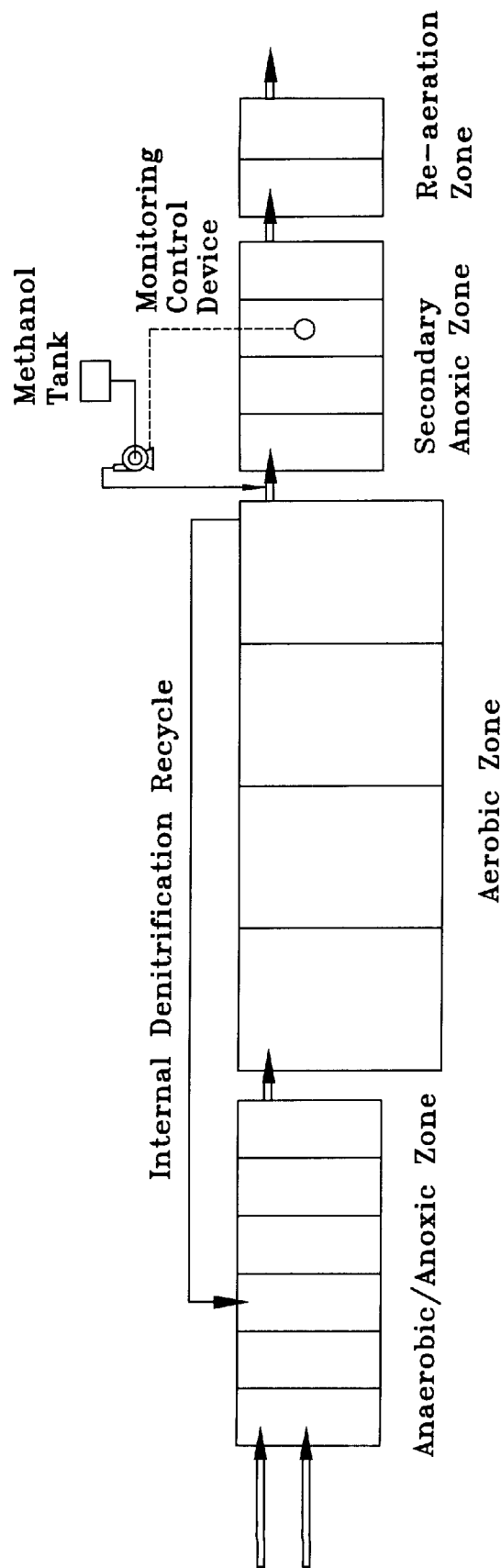
FIG. 7 is a schematic diagram of a five-stage Bardenpho process.

A preferred application of this invention is to monitor and control methanol addition to the secondary anoxic zone in a five-stage Bardenpho process. FIG. 7 represents a schematic of a five-stage Bardenpho system with the monitor/controller of the invention installed in the third tank of the secondary anoxic zone. The methanol pump is directly controlled by the monitor/controller and methanol is added to the front of the secondary anoxic zone. This monitor/controller produces a parameter sometimes hereinafter referred to as "denitrification time" or "DNT." In simple terms, DNT is the time required for the mixed liquor in the sample container to finish denitrification at the given ambient conditions. Specifically, when a mixed liquor sample is taken into the container and kept isolated with proper stirring, the microorganisms consume the nitrate and other carbonaceous nutrient in the water phase. The metabolic state of the microorganisms shifts from anoxic to anaerobic as the nitrate is fully depleted in the water phase. This phenomenon is shown in FIGS. 3–6 and 8–10. The time from when the sample is taken until nitrate is consumed is defined as denitrification time (DNT). Outside the sample container, the denitrification process progresses in the treatment tank simultaneously with the wastewater flowing through the treatment process. The average time that the mixed liquor spends in a wastewater treatment tank is called hydraulic retention time (HRT). HRT is generally defined as the volume of the treatment tank(s) divided by the total flow rate of mixed liquor to the tank(s) and is easily determined by standard methods well known in the art.

The comparison of DNT with HRT can provide an evaluation of the denitrification process. For example, a sample may be taken at the very front of an anoxic zone, which may include several anoxic tanks in series with an HRT equal to 25 minutes and the measured DNT is 30 minutes. The measurement of DNT indicates that it would take 30 minutes to finish denitrification in the anoxic zone. Since the mixed liquor stays in the anoxic zone for only 25 minutes, the conclusion would be that denitrification is not finished in the anoxic zone since DNT is longer than HRT. If the sample is taken from the middle of an anoxic zone, the HRT would be calculated from the section of sampling to the end of the anoxic zone.

Considering the same treatment process as in the above-mentioned example, that the sample is taken at the middle of the anoxic zone with remaining HRT equal to 12.5 minutes and the measured DNT is 17.5 minutes, the difference between DNT and HRT is still 5 minutes, with incomplete denitrification. As the location of the sampling changes, so does the measured DNT. However, as long as the correct HRT is selected to compare with DNT, the comparison will be valid. In general, if DNT is longer than HRT, denitrification is not finished; if DNT is shorter than HRT, denitrification is finished too early; if DNT and HRT are close, denitrification is finished as the mixed liquor leaves the anoxic zone.

In a five-stage Bardenpho system, the measured DNT is compared with the HRT of the mixed liquor in the remaining tank(s) of the anoxic zone (in this case, the fourth tank). The analysis and decision making operation of the monitor/controller is fundamentally separated into three groups.

Figure 8:
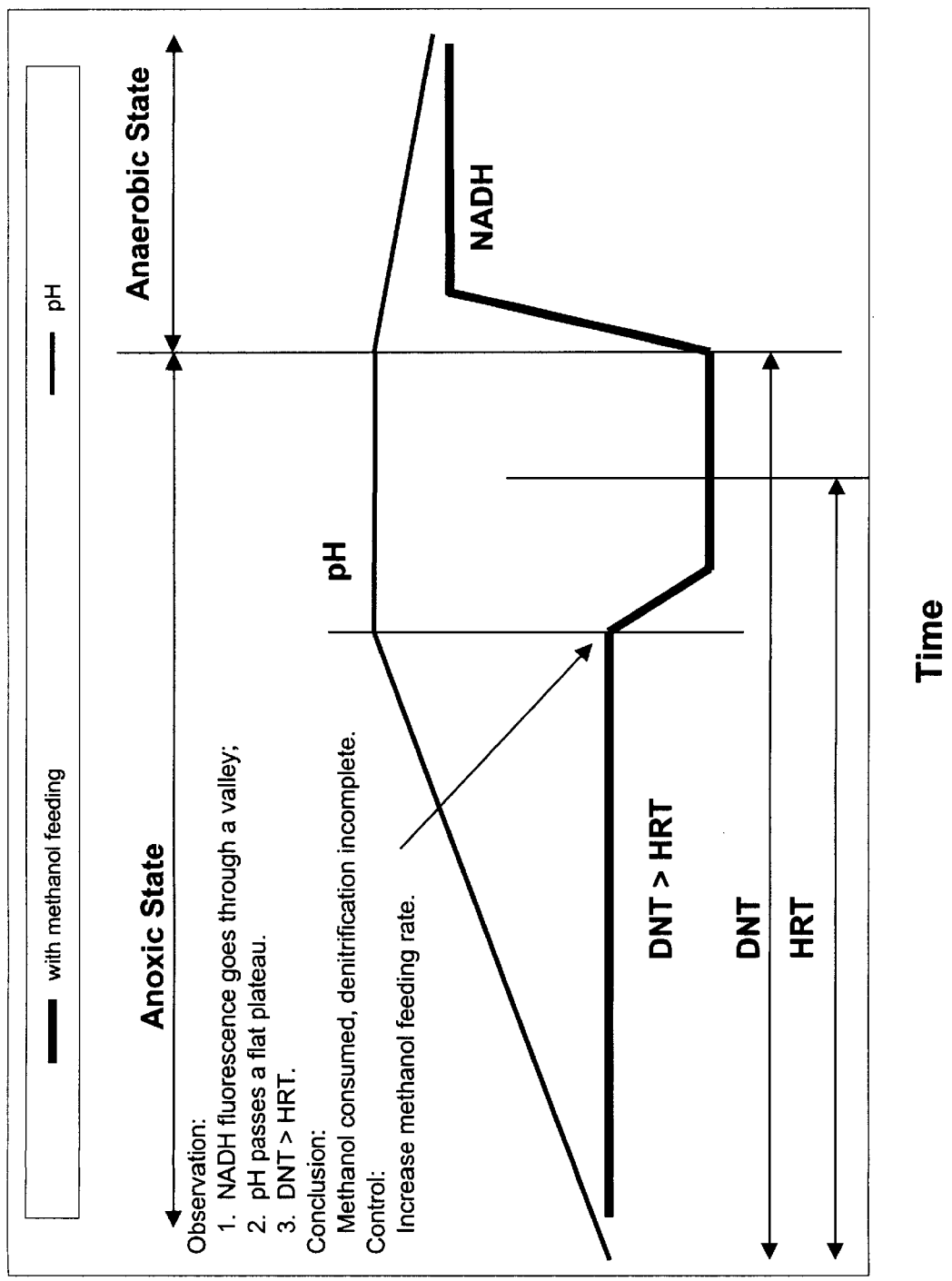
FIG. 8 is a graph of NADH and pH versus time in the anoxic and anaerobic states in a typical wastewater treatment process.

The condition of group one is represented in FIG. 8. The observations during the measurement are (1) NADH fluorescence proceeds through a valley; (2) pH passes a flat plateau; and (3) the measured DNT is much longer than HRT. The conclusion from this measurement cycle is that methanol is consumed earlier than the total consumption of $NO_x$, and denitrification is not finished in the anoxic zone. Consequently, the feeding rate of methanol should be increased to improve the denitrification process. As the methanol feeding rate increases, the denitrification rate increases due to the availability of carbonaceous nutrient throughout the denitrification process. Thus, the required denitrification time decreases, so that the measured DNT is close to the HRT in the anoxic tank(s). The denitrification process is optimized.

Figure 9:
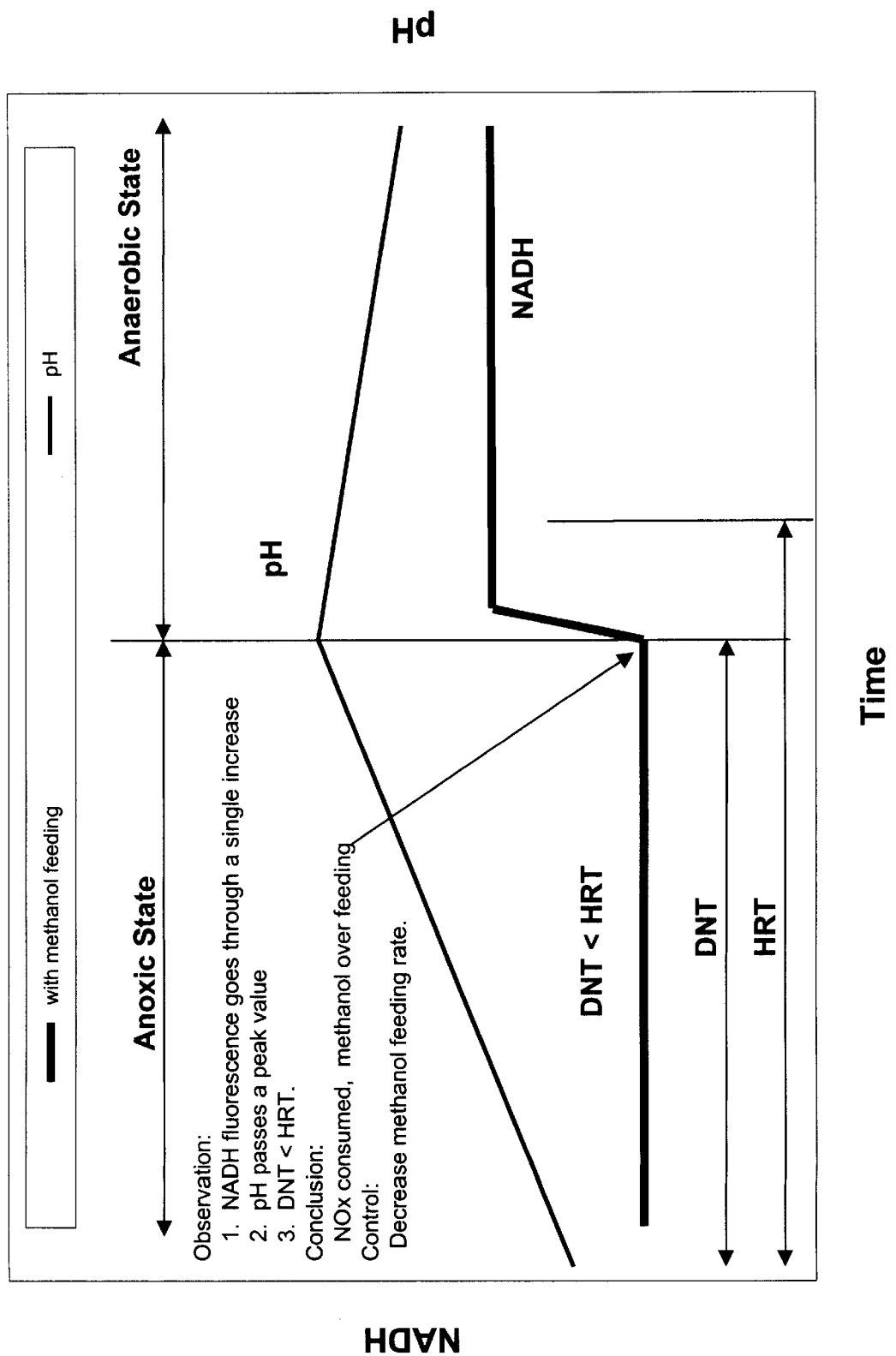
FIG. 9 is a graph of NADH versus time in the anoxic and anaerobic states in a typical wastewater treatment process.

The condition of group two is represented in FIG. 9. The observations during the measurement are (1) NADH fluorescence proceeds through a single stepwise increase; (2) pH passes a peak value; and (3) the measured DNT is much shorter than HRT. The conclusion from this measurement cycle is that denitrification is finished before the mixed liquor leaves the anoxic zone and the methanol feeding rate is too high. There is, as a result, possible leftover methanol. Consequently, the feeding rate of methanol should be reduced to optimize the denitrification process. As the methanol feeding rate decreases, the denitrification rate decreases due to the limitation of carbonaceous nutrient at the end of the denitrification process. Thus, the required denitrification time increases, so that the measured DNT is close to the HRT in the anoxic tank(s). The denitrification process is optimized.

Figure 10:
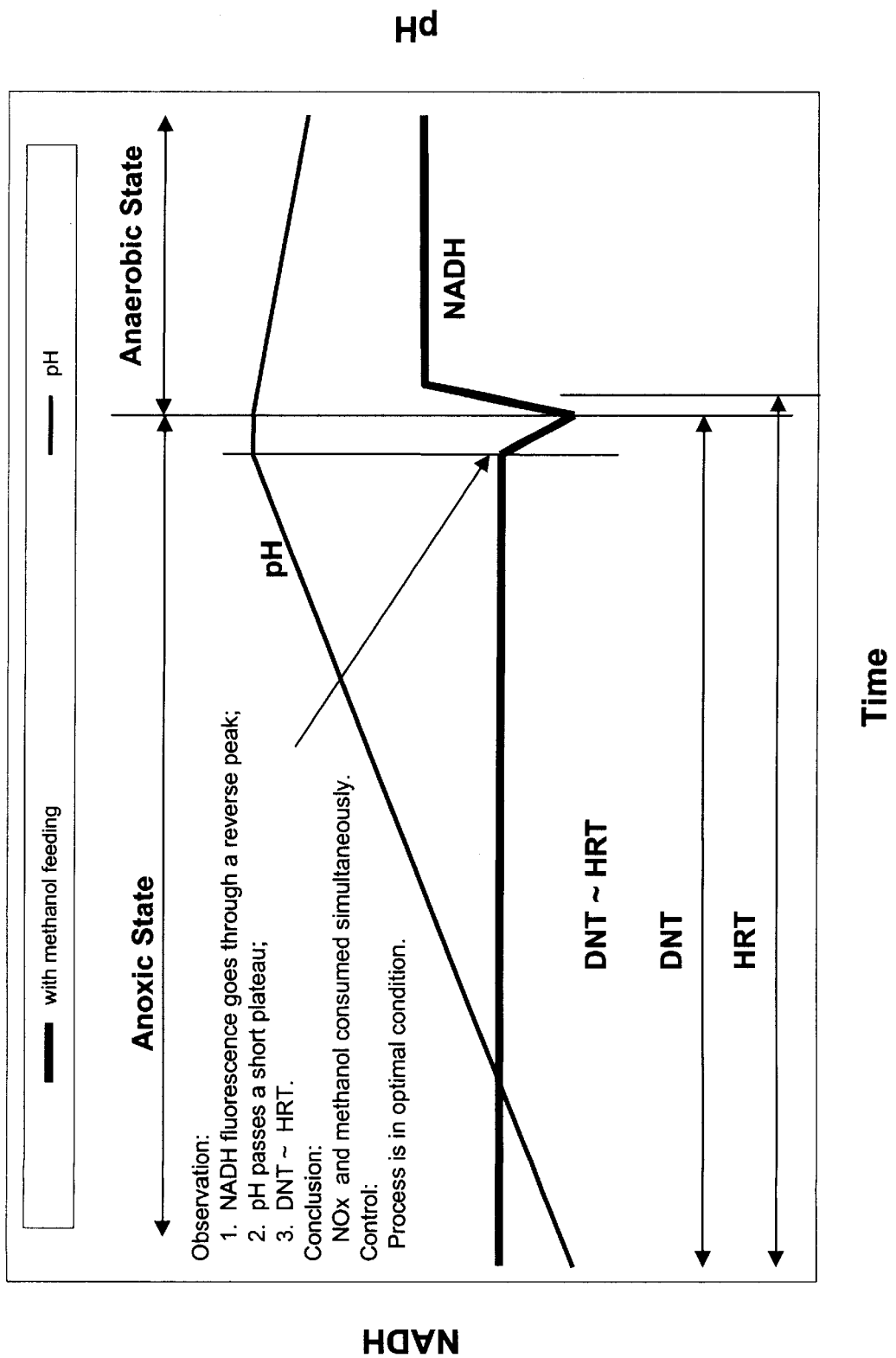
FIG. 10 is another graph of NADH versus time in the anoxic and anaerobic states in a typical wastewater treatment process.

The condition of group three is represented in FIG. 10. The observations during the measurement are (1) NADH fluorescence proceeds through a reverse peak; (2) pH passes a short plateau; and (3) the measured DNT is close to HRT. The conclusion from this measurement cycle is that $NO_x$ and methanol are consumed substantially simultaneously at the end of the anoxic zone. Therefore, the denitrification process is at an optimal condition.

What is claimed is:

1. A method of determining denitrification time for at least a portion of wastewater in a wastewater treatment process comprising:

isolating a wastewater sample from said wastewater in said wastewater treatment process;

detecting changes in fluorescence emitted by NADH from microorganisms contained within said sample;

detecting changes in pH of said sample;

analyzing said changes in NADH and pH and establishing that said sample is denitrified at a point where NADH shifts from a steady state or a decreasing state to an increasing state and, substantially simultaneously, said pH shifts from a steady state or an increasing state to a decreasing state; and calculating elapsed time between when said sample was taken and when said sample was denitrified to determine the denitrification time for said portion of said wastewater treatment process.

2. A method of monitoring denitrification of wastewater in a wastewater treatment process comprising:

isolating a wastewater sample from said wastewater in said wastewater treatment process;

detecting changes in fluorescence emitted by NADH from microorganisms contained within said sample;

detecting changes in pH of said sample;

analyzing said changes in NADH and pH and establishing that said sample is denitrified at a point where NADH shifts from a steady state or a decreasing state to an increasing state and, substantially simultaneously, said pH shifts from a steady state or an increasing state to a decreasing state;

calculating elapsed time between when said sample was taken and when said sample was denitrified to determine the denitrification time for said portion of said wastewater treatment process;

calculating a hydraulic retention time for said wastewater; and comparing said hydraulic retention time to said denitrification time.

3. The method defined in claim 2 further comprising adjusting the rate of carbonaceous nutrient feeding of said wastewater in response to said comparing.

4. The method defined in claim 3 wherein said adjusting is a reduction in said rate when the denitrification time is shorter than the hydraulic retention time.

5. The method defined in claim 3 wherein said adjusting is an increase in said rate when the denitrification time is longer than the hydraulic retention time.

6. A method of controlling denitrification of wastewater in a wastewater treatment process comprising:

isolating a wastewater sample from said wastewater in said wastewater treatment process;

detecting changes in fluorescence emitted by NADH from microorganisms contained within said sample;

detecting changes in pH of said sample;

calculating a hydraulic retention time for said wastewater;

analyzing said changes in NADH and pH and establishing that said sample is denitrified at a point where 1) NADH fluorescence proceeds through a valley and pH passes through a substantially flat plateau, 2) NADH fluorescence proceeds through a single stepwise increase and pH passes a peak or 3) NADH fluorescence proceeds through a reverse peak and pH passes through a substantially flat plateau;

calculating elapsed time between when said sample was taken and when said sample was denitrified according to any of 1), 2) and 3) to determine a denitrification time;

comparing said denitrification time to said hydraulic retention time; and adjusting the rate of carbonaceous nutrient feeding of said wastewater in response to said comparing as follows:
   i) increasing said feeding if the denitrification time calculated according to 1) is longer than said hydraulic retention time;
   ii) decreasing said feeding if the denitrification time calculated according to 2) is shorter than said hydraulic retention time; and
   iii) maintaining said feeding substantially constant if the denitrification time calculated according to 3) is about the same as the hydraulic retention time.

* * * * *